:

US005501985A

United States Patent [19]
Baugher et al.

[11] Patent Number: 5,501,985
[45] Date of Patent: *Mar. 26, 1996

[54] ANALYTE-SUBSTITUTE REAGENT FOR USE IN SPECIFIC BINDING ASSAY METHODS, DEVICES AND KITS

[75] Inventors: Bennett W. Baugher, Waukegan; Aurora J. Chamberlain, Buffalo Grove; Sharon M. Devereaux, Gurnee; Frank S. Ungemach, Lake Villa, all of Ill.

[73] Assignee: Abbott Laboratories, Abbott Park, Ill.

[ * ] Notice: The term of this patent shall not extend beyond the expiration date of Pat. No. 5,340,748.

[21] Appl. No.: 230,995

[22] Filed: Apr. 21, 1994

Related U.S. Application Data

[63] Continuation of Ser. No. 67,254, May 25, 1993, Pat. No. 5,340,748, which is a continuation of Ser. No. 554,304, Jul. 18, 1990, abandoned.

[51] Int. Cl.$^6$ .................................................. G01N 33/543
[52] U.S. Cl. .............................. 436/518; 422/50; 422/56; 422/60; 435/7.93; 435/971; 435/973; 435/975; 436/514; 436/538; 436/540; 436/816; 436/817; 436/822

[58] Field of Search ..................... 436/514, 518, 436/537, 538, 540, 816, 817, 822, 839, 841; 422/50, 56, 60; 435/7.92, 7.93, 971, 973, 975

[56] References Cited

U.S. PATENT DOCUMENTS

| | | | |
|---|---|---|---|
| 4,446,232 | 5/1984 | Liotta | 435/7.93 |
| 4,496,654 | 1/1985 | Katz et al. | 435/805 X |
| 4,803,170 | 7/1989 | Stanton et al. | 436/518 |
| 5,340,748 | 8/1994 | Baugher et al. | 436/518 |

*Primary Examiner*—Toni R. Scheiner
*Assistant Examiner*—Susan C. Wolski
*Attorney, Agent, or Firm*—Gregory W. Steele

[57] ABSTRACT

Assay reagents, devices, methods and kits used in the analysis of low molecular weight analytes which by themselves are too small or unable to bind to two specific binding members at the same time. The invention involves the use of an analyte-substitute reagent (ASR) comprising at least two components, the first of which is identical to or an analog of the analyte to be determined, while the second is an unrelated ligand for which an antibody or other specific binding member can be obtained or produced.

4 Claims, No Drawings

ANALYTE-SUBSTITUTE REAGENT FOR USE IN SPECIFIC BINDING ASSAY METHODS, DEVICES AND KITS

This is a continuation of application Ser. No. 08/067,254, filed May 25, 1993, now U.S. Pat. No. 5,340,748, which is a file wrapper continuation of Ser. No. 07/554,304, filed Jul. 18, 1990, abandoned.

BACKGROUND OF THE INVENTION

1. Field of the Invention

The invention relates generally to the field of diagnostic assays. More particularly, the present invention relates to the use of an analyte-substitute reagent in a binding assay to form a detectable binding member complex, wherein that detectable complex correlates to the presence or amount of analyte in the test sample.

2. Description of Related Art

Various analytical procedures and devices are commonly employed in assays to determine the presence and/or concentration of substances of interest or clinical significance which may be present in biological fluids or other materials. Such substances are commonly termed "analytes" and can include antibodies, antigens and haptens. In the diagnosis and treatment of disease or other conditions of the human body, the accurate and timely determination of the presence or amount of an analyte in a biological sample can have a profound influence on the ability of health care professionals to treat and manage a pathological disorder. In addition, the performance of such assays enables early and accurate determination of physiological conditions such as pregnancy, the monitoring of drug therapy and the evaluation of the absence, presence and amount of drugs of abuse or toxins.

Typical immunoassay techniques utilize the mechanisms of the immune systems of higher organisms, wherein antibodies are produced in response to the presence of antigens which are pathogenic or foreign to the organisms. One or more antibodies are produced in response to and are capable of reacting with a particular antigen, thereby creating a highly specific reaction mechanism which can be used in vitro to determine the presence or concentration of that particular antigen in a biological sample.

Heterogeneous immunoassay techniques typically involve the use of a solid phase material to which the reaction product becomes bound. The reaction product is separated from excess sample, assay reagents and other substances by removing the solid phase from the reaction mixture. One type of solid phase immunoassay is a sandwich immunoassay involving an anti-analyte antibody (capture reagent) bound to the insoluble solid phase material, as described by Schuurs et al. U.S. Pat. Nos. 3,791,932 and 4,016,043. A second anti-analyte antibody is labeled with a detectable agent to form an indicator reagent, e.g., the detectable label can be an enzyme which will react with an enzyme substrate to form a detectable product. If the analyte is present in the test sample, then the two antibodies form an immunocomplex with the analyte (i.e., an antibody/analyte/antibody sandwich), and the amount of indicator reagent associated with the solid phase is directly proportional to the amount of analyte in the test sample. When the enzyme substrate is added, it reacts with the enzyme component of the indicator reagent to signal the presence or amount of analyte associated with the solid phase.

Another type of solid phase immunoassay configuration is the competitive assay. In a manner similar to the sandwich assay, the competitive assay can involve an anti-analyte antibody bound to the insoluble solid phase, but a labeled analyte, instead of a labeled second antibody, may be used as the indicator reagent. In the competitive assay, the indicator reagent competes with the test sample analyte to bind the capture reagent on the solid phase. The amount of captured indicator reagent is inversely proportional to the amount of analyte present in the test sample. Smith (U.S. Pat. No. 4,401,764) describes an alternative competitive assay format using a mixed binding complex which can bind analyte or labeled analyte but wherein the analyte and labeled analyte can not simultaneously bind the complex. Clagett (U.S. Pat. No. 4,746,631) describes an immunoassay method using a reaction chamber in which an analyte/ligand/marker conjugate is displaced from the reaction surface in the presence of test sample analyte and in which the displaced analyte/ligand/marker conjugate is immobilized at a second reaction site. The conjugate includes biotin, bovine serum albumin and synthetic peptides as the ligand component of the conjugate, and enzymes, chemiluminescent materials, enzyme inhibitors and radionucleotides as the marker component of the conjugate. Li (U.S. Pat. No. 4,661,444) describes a competitive immunoassay using a conjugate of an anti-idiotype antibody and a second antibody, specific for a detectable label, wherein the detectable response is inversely related to the presence of analyte in the sample.

In both the sandwich and competitive immunoassays, the presence or amount of analyte in the test sample is generally determined by detecting the presence or amount of the label which has become associated with the solid phase. In the competitive assay, the more analyte present in the test sample the lower the amount of label present on the solid phase. In the sandwich assay, the more analyte present in the sample the greater the amount of label present on the solid phase. The sandwich assay is generally preferred, especially for the visualization of low analyte concentrations, because the appearance of label on the solid phase is more readily detected.

The sandwich assay, however, is subject to several limiting factors. Certain analytes of interest, such as some steroids, hormones, antibiotics and other therapeutic drugs, have a low molecular weight and a corresponding size that is too small to allow the simultaneous binding of two antibodies to the analyte and thereby form the sandwich complex. Methods for detecting such analytes typically use a competitive assay configuration wherein the analyte either competes with an indicator reagent for binding to a capture reagent or wherein the analyte displaces the indicator reagent from the capture reagent. A positive result in a displacement assay is indicated by a decrease in the amount of label associated with the solid phase material. Visually determining a positive assay result by detecting a decreasing amount of label is more difficult than detecting the appearance of label on the solid phase, and difficulty in discerning a decrease in the amount of label can lead to ambiguity in the interpretation of the assay result. Allen (EP 177,191) describes a binding assay involving a conjugate of a ligand analog and a second reagent, such as fluorescein, wherein the conjugate competes with the analyte (ligand) in binding to a labeled binding partner specific for the ligand, and wherein the resultant labeled conjugate is then separated from the reaction mixture by means of solid phase carrying a binding partner for the second reagent. This binding assay format combines the use of a competitive binding technique and a reverse sandwich assay configuration, i.e., the binding of conjugate to the labeled binding member prior to separating conjugate from the mixture by the binding of the conjugate to the solid phase. The assay result, however, is determined as in a conventional competitive assay wherein the amount of label bound to the solid phase is inversely proportional to the amount of analyte in the test sample. Chieregatt et al. (GB 2,084,317) describe a similar assay format using an indirectly labeled binding partner specific for the analyte. Mochida et al. (U.S. Pat. No. 4,185,084) also describe the use of a double-antigen conjugate which competes with an antigen analyte for binding to an immobilized antibody and which is then labeled; this method also results in the detection of label on a solid phase wherein the amount of label is inversely proportional to the amount of analyte in the test sample. Sadeh et al. (U.S. Pat. No. 4,243,749) describe a similar enzyme immunoassay wherein a hapten conjugate competes with analyte for binding to an antibody immobilized upon a solid phase.

SUMMARY OF THE INVENTION

The present invention provides an analyte-substitute reagent (ASR), assay methods, devices and test kits for performing binding assays which are especially useful for determining the presence or amount of analytes of small molecular size. The ASR is capable of reacting with suitable assay reagent binding members and thereby form detectable ASR complexes or free ASR in amounts proportional to the amount of analyte in the test sample. In one embodiment of the present invention, the ASR may replace the analyte in the formation of detectable complexes. In other embodiments, the ASR may be used to form detectable complexes which the analyte of interest could not form due to size, steric hindrance or epitope limitations.

In yet other embodiments, the ASR substitutes for the analyte in the formation of a detectable binding member complex, wherein the presence of detectable complex on a solid phase is directly proportional to the presence of analyte in the test sample. Such an advantageous direct result is achieved by concurrent use of an analyte-specific binding member which is reacted with the analyte and the ASR to competitively form analyte/binding member complex and ASR/binding member complex. The amount of uncomplexed ASR which remains is then directly proportional to the amount of analyte in the test sample. The uncomplexed ASR then serves as a substitute for analyte in the formation of a detectable sandwich assay complex.

The ASR comprises a first component which is an analyte, analyte-analog or other ligand having at least one epitope in common with the analyte, thereby enabling the ASR to bind to an analyte-specific binding member, and a second component which is a ligand that selectively reacts with a ligand-specific binding member but which is not reactive with the analyte-specific binding member (nor is the ligand-specific binding member reactive with the analyte-specific binding member).

The method for determining the presence or amount of an analyte in a test sample involves contacting the test sample with the following reagents: an ASR; a first specific binding member capable of binding to an epitope which the test sample analyte and the analyte-component of the ASR have in common; a capture reagent comprising a second specific binding member which is specific for the ligand-component of the ASR; and an indicator reagent comprising a third binding member specific for the analyte-component of the ASR and a label capable of producing a detectable signal. In such an assay, the first and third specific binding members may be the same. Alternatively, the second specific binding member of the capture reagent can be specific for the analyte-component of the ASR and the third specific binding member of the indicator reagent can be specific for the ligand-component of the ASR. The test sample can be contacted to the assay reagents sequentially, singly or in combination. The assay method can also include contacting the label of the indicator reagent with at least one additional signal generating substance which is capable of reacting with the label to produce the detectable signal.

In the assay, the ASR and the analyte of the test sample compete in binding to the first specific binding member, with the free or unbound ASR serving to complete the formation of a sandwich complex with the capture and indicator reagents. The label associated with the complex, or the amount of indicator reagent that is not associated with the complex, is then detected to determine the presence or amount of analyte in the test sample.

Variations of the present invention include embodiments wherein the first specific binding member and the ASR are present as a tablet, capsule, powder or liquid reagent configuration to which the test sample is added; device embodiments wherein the capture reagent is immobilized on a solid phase material so that the resultant sandwich complex is immobilized on the solid phase material; embodiments wherein the assay method includes the step of immobilizing the capture reagent on a solid phase material; embodiments wherein the assay method includes the addition of at least one ancillary specific binding member to complete the assay reaction, the sandwich complex or the immobilization of the capture reagent; and embodiments wherein multiple analytes are assayed on the solid phase material using multiple ASRs. Typically, the immobilized capture reagent serves as the detection site for the sandwich complex in assay devices. Devices are contemplated, however, wherein the detection of the indicator reagent takes place at a site other than or in addition to the immobilized capture reagent site.

A further variation of the present invention involves the use of a preformed binding complex comprising the ASR, a capture reagent and an indicator reagent. With the addition of the test sample, the analyte of the test sample is believed to replace the ASR in indicator reagent binding, resulting in the detectable displacement of the indicator reagent from the complex.

The present invention also involves test kits for determining the presence or amount of an analyte in a test sample. The kits comprise an ASR and other reagents required for the desired binding assay. Furthermore, the present invention includes assay devices, especially those allowing the production of self-performing assays, i.e., the solid phase can include a sufficient number of zones or layers to contain the assay reagents in a configuration whereby the assay is substantially self-performing upon the addition of test sample.

A further aspect of the present invention is the addition of a surfactant to the indicator reagent either during production of the indicator reagent or prior to the use of the indicator reagent in an assay. The addition of a surfactant significantly improves the performance of the indicator reagent and can even revive indicator reagents that appear inactive or that have diminished activity.

DETAILED DESCRIPTION OF THE INVENTION

The present invention involves assay methods and test kits for performing solid phase assays using an ASR which is capable of forming a detectable binding member complex which corresponds to the presence or amount of analyte in the test sample. The ASR comprises a first component having at least one epitope in common with the analyte of interest, thereby enabling the first component to bind to an analyte-specific binding member, and a second component which is a ligand that selectively interacts with a ligand-specific binding member but which is not reactive with the analyte-specific binding member.

The following terms are used herein in accordance with the known art involving binding assays.

The term "specific binding member" refers to a member of a specific binding pair, i.e., two different molecules wherein one of the molecules, through chemical or physical means, specifically binds to the second molecule. In addition to antigen and antibody specific binding pairs, other specific binding pairs include, as examples without limitation, biotin and avidin, carbohydrates and lectins, complementary nucleotide sequences, complementary peptide sequences, effector and receptor molecules, enzyme cofactors and enzymes, enzyme inhibitors and enzymes, a peptide sequence and an antibody specific for the sequence or the entire protein, polymeric acids and bases, dyes and protein binders, peptides and specific protein binders (e.g., ribonuclease, S-peptide and ribonuclease S-protein), and the like. Furthermore, specific binding pairs can include members that are analogs of the original specific binding member, for example an analyte-analog. If the specific binding member is an immunoreactant it can be, for example, an antibody, antigen, hapten, or complex thereof, and if an antibody is used, it can be a monoclonal or polyclonal antibody, a recombinant protein or antibody, a mixture(s) or fragment(s) thereof, as well as a mixture of an antibody and other specific binding members. The details of the preparation of such antibodies and their suitability for use as specific binding members are well known to those skilled in the art.

The term "analyte" refers to the compound or composition to be detected or measured, which has at least one epitope or binding site. The analyte can be any substance for which there exists a naturally occurring analyte-specific binding member or for which an analyte-specific binding member can be prepared. Analytes include, but are not limited to toxins, organic compounds, proteins, peptides, amino acids, nucleic acids, hormones, steroids, vitamins, drugs (including those administered for therapeutic purposes as well as those administered for illicit purposes), and metabolites of or antibodies to any of the above substances. The term "analyte" also includes any antigenic substances, haptens, antibodies, and combinations thereof which are of interest in immunoassays. The reagents and methods of the present invention can also be designed to determine food product and environmental analytes of interest.

The term "analyte-analog" refers to a substance which cross-reacts with the analyte-specific binding member, although it may do so to a greater or a lesser extent than does the analyte itself. The analyte-analog can include a modified analyte as well as a fragmented or synthetic portion of the analyte molecule or a substantially different ligand so long as the analyte-analog has at least one epitopic site in common with the analyte of interest. An example of an analyte-analog is a synthetic peptide sequence which duplicates at least one epitope of the whole-molecule analyte so that the analyte-analog can bind to the analyte-specific binding member.

The term "ligand" refers to any substance for which a ligand-specific binding member naturally exists or can be prepared, but it is a substance not typically found in a test sample, or at least it is not present in an amount that would noticeably interfere with the binding of the ASR or the detection or measurement of the the analyte of interest. Similarly, the ligand-specific binding member is a substance not typically found in a test sample.

The term "ancillary specific binding member" refers to a specific binding member which is used in the assay in addition to the specific binding members of the capture reagent and the indicator reagent. One or more ancillary specific binding members can be used in an assay. For example, an ancillary specific binding member can be used to complete the formation of a binding complex between the analyte-component of the ASR and the indicator reagent. Alternatively, an ancillary specific binding member can be used to immobilize the capture reagent upon a solid phase material through a binding reaction that is ancillary to the completion of the sandwich complex. Thus, an ancillary specific binding member can be readily used to directly or indirectly attach an assay reagent to the ASR, a solid phase or a label.

The term "test sample" typically refers to a naturally occurring or artificially formed liquid test medium suspected of containing the analyte of interest. The test sample is generally a biological fluid or a dilution thereof. Biological fluids from which an analyte can be determined include serum, whole blood, plasma, urine, saliva, amniotic and cerebrospinal fluids, and the like, and includes such fluids after treatment with extraction, dilution or other sample treatment solutions. The test sample can also include a solid material (e.g., hair, tissue, etc.) which has been modified to form a liquid test medium.

REAGENTS AND MATERIALS

Typically, the binding assays of the present invention use an indicator reagent to indicate the presence or amount of an analyte in a test sample and a capture reagent, directly or indirectly attached to a solid phase material, to separate the binding reaction complex from the test sample and assay reagents for ease of observation. Additional materials can be used depending on the desired assay method.

Indicator Reagent

The indicator reagent typically includes a label and a specific binding member. The indicator reagent is capable of producing a detectable signal that can be correlated to the presence or amount of analyte in the test sample. In general, the indicator reagent is detected or measured after immobilization upon a solid phase material, but free or unbound indicator reagent can also be detected or measured to determine the result of an assay. The specific binding member of the indicator reagent can be a member of any specific binding pair as described above. The label of the indicator reagent is a substance capable of producing a signal detectable by visual or instrumental means.

Suitable labels for use in the present invention include chromogens; catalysts; fluorescent compounds; chemiluminescent compounds; radioactive isotopes; direct visual labels including colloidal metallic and non-metallic particles, dye particles, enzymes or substrates, or organic polymer latex particles; liposomes or other vesicles containing signal producing substances; and the like.

A large number of enzymes suitable for use as labels are disclosed in U.S. Pat. No. 4,275,149, columns 19–23, herein incorporated by reference. For example, an enzyme/substrate signal producing system useful in the present invention is the enzyme alkaline phosphatase wherein the substrate used is nitro blue tetrazolium-5-bromo-4-chloro-3-indolyl phosphate or a derivative or analog thereof.

In an alternative signal producing system, the label can be a fluorescent compound where no enzymatic manipulation of the label is required to produce a detectable signal. Fluorescent molecules such as fluorescein, phycobiliprotein, rhodamine and their derivatives and analogs are suitable for use as labels in this reaction.

In preferred assay methods, a visually detectable, colored particle is used as the label, thereby providing for a direct colored readout of the presence or concentration of the analyte in the test sample without the need for the addition of further signal producing reagents. Materials used as colored particles include colloidal metals, such as gold, and dye particles as disclosed in U.S. Pat. Nos. 4,313,734 and 4,373,932, which are herein incorporated by reference. The preparation and use of non-metallic colloids, such as colloidal selenium particles, are disclosed in co-owned and copending U.S. patent application Ser. No. 072,084, filed Jul. 9, 1987, herein incorporated by reference. The use of colloidal particle labels in immunochromatography is disclosed in co-owned and copending U.S. patent application Ser. No. 072,459, filed Jul. 13, 1987, herein incorporated by reference. Organic polymer latex particles for use as labels are disclosed in co-owned and copending U.S. patent application Ser. No. 248,858, filed Sep. 23, 1988, herein incorporated by reference.

The selection of a particular label is not critical to the present invention, so long as the selected label is capable of generating a detectable signal either by itself or in conjunction with one or more additional substances. A variety of different indicator reagents can be formed by varying either the label or the specific binding member.

Capture Reagent

The capture reagent of the present invention is a specific binding member which is typically affixed to a solid phase material. In general, the immobilized capture reagent serves to immobilize the assay reaction product for detection and/or measurement upon the solid phase material. The capture reagent can be any substance capable of specifically binding with another. The capture reagent includes binding members that are capable of binding to the analyte component of the ASR, the ligand component of the ASR or an ancillary specific binding member.

The present invention can also include a capture reagent that is not initially attached to a solid phase material. Once complex formation occurs between the assay reagents, the solid phase can be used as a separation mechanism: the reaction mixture is contacted with the solid phase material, and the newly formed sandwich complex(es) are retained by the solid phase material. Alternative methods can be used to perform this separation step, such as using a solid phase which itself binds the capture reagent; affixing to the solid phase a binding member that is specific for the capture reagent; or affixing to the solid phase a reactive agent, such as a charged substance, which will attract and bind an oppositely charged substance that has been bound to the capture reagent, as disclosed in co-owned and copending U.S. patent application Ser. No. 150,278, filed Jan. 29, 1988, herein incorporated by reference. Precipitation or agglutination assays are also contemplated using the ASR and novel assay format of the present invention.

The assay device of the present invention can have many configurations, several of which are dependent upon the material chosen for the solid phase. Frequently, the solid phase material is any suitable chromatographic, bibulous, porous or capillary material. In the present invention, the solid phase material can include a fiberglass, cellulose or nylon pad for use in a flow-through assay device having one or more layers containing one or more of the assay reagents; a dipstick for a dip and read assay; a test strip for chromatographic (e.g., paper or glass fiber) or thin layer chromatographic (e.g., nitrocellulose) techniques in which one or more reagents are contained in separate or nonoverlapping zones of a single strip of solid phase material; or an absorbent or film material well known to those skilled in the art. The solid phase material can also include, without limitation, polyacrylamide beads, polystyrene beads or tubes, magnetic beads, a microtitre plate or a glass or plastic test tube, or other solid material such as a sheet, slide or plate having a smooth surface, wells or channels.

Natural, synthetic or naturally occurring materials that are synthetically modified, can be used as a solid phase material including polysaccharides, e.g., cellulose materials including paper, cellulose and cellulose derivatives such as cellulose acetate and nitrocellulose; silica; fiberglass; inorganic materials such as deactivated alumina, diatomaceous earth or other inorganic finely divided material uniformly dispersed in a porous polymer matrix, with polymers such as vinyl chloride, vinyl chloride-propylene copolymer, and vinyl chloride-vinyl acetate copolymer; cloth, both naturally occurring (e.g., cotton) and synthetic (e.g., nylon); porous gels such as silica gel, agarose, dextran and gelatin; polymeric films such as polyacrylamide; magnetic particles; microtitre plates; polystyrene tubes; protein binding membranes; agarose; Sephadex® (Pharmacia Fine Chemicals, Inc., Piscataway, N.J.); Trisacryl® (Pointet-Girard, France); silicon particles; porous fibrous matrixes; and the like. The solid phase material should have a reasonable inherent strength, or strength can be provided by means of a separate support material.

The capture reagent of the present invention, however, is not limited to a specific binding member directly or indirectly bound to an insoluble solid phase material. In an agglutination assay, for example, the specific binding member of the capture reagent can be bound to a soluble carrier material such as bovine serum albumin.

Ancillary Materials

Although it is not critical to the present invention, the capture reagent also can be coated onto particles, e.g., "beads" or "microparticles" that can be filtered or retained and immobilized by an additional solid phase base material. By "retained and immobilized" is meant that the particles, once on the solid phase base material, are not capable of substantial movement to positions elsewhere within the material. The particles can be selected by one skilled in the art from any suitable type of particulate material such as those composed of polystyrene, polymethylacrylate, polyacrylamide, polypropylene, latex, polytetrafluoroethylene, polyacrylonitrile, polycarbonate or similar materials.

Another aspect of the present invention involves the addition of a surfactant to the indicator reagent. In some instances, the activity of the indicator reagent can diminish during storage. The addition of a surfactant to the indicator reagent dilution buffer significantly improves the performance of the indicator reagent and can even revive indicator reagents that appear inactive or that have greatly diminished activity. As a result of the improved performance of the surfactant-treated indicator reagent, the amount of indicator reagent necessary to perform an assay can sometimes be reduced.

The amount and type of surfactant used may vary with the specific binding member, label and coupling method used to form the indicator reagent. The effect of the surfactant on the stability of the specific binding member or the label's activity is important when selecting the appropriate type and amount of surfactant. Preferably, the surfactant type and amount will maintain the stability of the specific binding member and the label, will be compatible with the other assay reagents and will not affect the desired binding reactions of the assay reagents. Furthermore, the amount of surfactant necessary to maintain the indicator reagent's activity is generally less than the amount necessary to revive an inactive indicator reagent. Alternatively, if the long term stability of the indicator reagent is affected by exposure to the surfactant, then the surfactant may be added to the indicator reagent just prior to the reagent's use in the assay. Non-limiting examples of surfactants that may be used, individually or in combination, include alkylpyranosides, polyoxyethylenesorbitans (Tweens), polyoxyethylene ethers (e.g., Tritons®, Rohm & Haas Co.), polyglycol ethers (e.g., Tergitol®, Union Carbide Corp.), sorbitans (Spans), other nonionic detergents, anionic detergents (such as dodecyl sulfate salts), cationic detergents (such as alkylammonium salts) and zwitterionic detergents (such as Chaps).

The present invention further provides kits of reagents including the ASRs and the components for carrying out the assay methods of the invention. The kits can include unbound ASR or an ASR which is a part of a preformed complex further comprising one or more specific binding members.

ANALYTE-SUBSTITUTE REAGENT

The ASR has at least two components, the first of which is identical to or an analog of the analyte of interest, while the second is an unrelated ligand or nonanalyte. Thus, the first component of the ASR can be an analyte, such as a drug or drug analog, and the second component can be any substance or ligand other than the analyte so long as the substance is not typically present in free form in the test sample, or at least not present in an amount that will interfere with the assay reaction. It is also contemplated that the test sample may be treated prior to use for the removal of interfering ligands.

With the ASR of the present invention, a positive finding for an analyte having a single available epitope for binding is advantageously represented by the appearance of or an increase in signal, i.e., the detectable signal increases proportionately with the concentration of the analyte in the test sample. This is achieved because the ASR serves as a multiepitopic substitute for the analyte thereby enabling the formation of a detectable binding complex in direct proportion to the presence or amount of analyte in the test sample. The ASR provides at least two binding sites so that at least two additional binding members, e.g., capture reagent and indicator reagent, can bind to the ASR to form an immunocomplex that is indicative of the presence or amount of the analyte in the sample.

While the ASR is useful for determining the presence or amount of a wide range of analytes, including high molecular weight analytes (4,000 to 2,000,000), it is particularly well suited for determining the presence or amount of analytes of low molecular weight, such as analytes within the molecular weight range of 50 to 4,000. The present invention is especially advantageous for determining the presence or amount of analytes having molecular weights in the range of 100 to 2,000, including steroids, vitamins, prostaglandins, antiasthmatic drugs, antiarrythmic drugs, antineoplastic drugs, anticonvulsant drugs, antibiotics, antiarthritic drugs, antidepressant drugs, and drugs of abuse such as cocaine, morphine, heroin, amphetamine, methamphetamine, cannabinoids and the like.

The problem encountered by conventional assays for many of these low molecular weight analytes is that the analytes are too small to allow the binding of two binding members to an analyte at the same time. The sandwich assay format requires the presence of at least two binding sites or epitopes on the analyte molecule, with sufficient distance between these two binding sites to allow two binding members to simultaneously bind to the analyte without steric interference.

Low molecular weight, however, is not the only parameter for determining which analytes are particularly suited for analyses by the present invention. For example, a compact molecule may actually be heavier than a non-compact molecule even though both have the same length in their longest dimension. Furthermore, the analyte might have two epitopes suitable for binding the antibodies, but the epitopes may not be located at the two points on the analyte molecule that are a sufficient distance from each other to allow binding without steric hindrance. Or, certain analytes such as haptens may have only a single accessible binding site. Therefore, the utility of the present invention is not limited to low molecular weight analytes, even though molecular weight is used in the description as illustrative of the types of molecules that are advantageously detected by means of the present invention.

In the present invention, the first component of the ASR is an analyte or analyte-analog, having at least one epitope in-common with the assay's analyte of interest. For example, the analyte-analog can be derived from the corresponding analyte by the removal of a reactive hydrogen atom (i.e., a hydrogen atom bonded to a hydroxy oxygen) or of a reactive amine (primary or secondary), or by the formation of an amino derivative of the analyte wherein an imino group replaces one or more atoms originally present in the analyte at the site of binding to the ligand component of the ASR. Other reactive groups include, but are not limited to, carboxylic acids, nitriles, halogens and the like. Substances illustrative of the analytes which upon removal of a reactive hydrogen may form analyte-analogs include procainamide, thyroxine and quinidine. Analytes whose amino derivatives are useful as analyte-analogs include theophylline, valproic acid, phenobarbital, phenytoin, primidone, disopyramide, digoxin, chloramphenical, salicylate, acetaminophen, carbamazepine, desipramine and nortriptyline. In addition, the analyte can undergo structural modification by the addition or deletion of one or more functional components or binding sites to form an analyte-analog, such as a partial peptide or nucleotide sequence which is a smaller sequence than the entire analyte sequence but which retains the necessary epitopic site(s) for binding to an analyte-specific binding member. For example, the analyte-analog can be a synthetic peptide sequence which has at least one epitope in common with the analyte.

The second or ligand component of the ASR generally includes, but is not limited to, avidin, biotin, fluorescein, a fluorescein derivative, rhodamine or a rhodamine derivative.

The fluorescein compounds can include: fluorescein amine; fluorescein thioisocyanate; carboxy fluorescein; α-iodoacetamidofluorescein; (2,3,-dichloro-1,3,5-triazin-2-ylamino)fluorescein (DTAF); (4-chloro-6-methoxy-1,3,5-triazin-2-ylamino) fluorescein; and aminomethyl fluorescein. If biotin is used as the ligand component of the ASR, its complementary specific binding member can be avidin or an anti-biotin antibody. When the ligand component of the ASR is fluorescein or a fluorescein derivative, the preferred specific binding member for the ligand is an antifluorescein antibody. Fluorescein is especially advantageous for use as the ligand-component of the ASR because antibodies to fluorescein are readily available. It is contemplated, however, that the ligand component of the ASR can be virtually any specific binding member as discussed above, which does not interfere with assay reagent and analyte binding. Thus, the ligand component could be another antigen, an antibody, a peptide sequence, a nucleotide sequence, etc. that is not related to the analyte or analyte-specific binding member.

In the present invention, the two components of the ASR can be irreversibly attached. Various molecular bridges or linking groups can also be used to attach the analyte component to the ligand component. For example, the linking group between an analyte-analog and a fluorescein derivative can include up to seven heteroatoms and a total of from 0 to 20 carbon atoms and heteroatoms arranged in a straight or a branched chain and containing up to two ring structures. Considerations for choosing the type of linking mechanism used to form the ASR are that the linking of the ligand to the analyte or analyte-analog must not interfere with either component's ability to bind with its respective specific binding partner, and the linking mechanism must not interfere with the ability of the ASR to form a binding member complex.

In an assay device or kit, the ASR can initially be supplied as a reagent that is reversibly joined to a first specific binding member, wherein the test sample analyte displaces the ASR due to the analyte's competitive binding to the first specific binding member. Typically, both the ASR and the first specific binding member are present without being coupled or bound prior to the assay procedure. The ASR/first specific binding member complex or mixture can have a variety of configurations, such as a lyophilized powder, a tablet, a capsule or a fluid reagent.

DIAGNOSTIC ASSAYS

The ASR can be used in a variety of binding assay configurations, and the following methods for using the present invention are intended to be descriptive but not limitative of the invention. Typically, the assays are "direct" assays in that the specific binding members of the indicator and capture reagents directly react with the ASR to form a binding complex. "indirect" assays are also contemplated using the present invention, for example, an assay wherein the specific binding member of the indicator is specific for an ancillary specific binding member, which in turn is specific for the ASR.

In addition, the assays can be performed in a variety of ways. Test sample, ASR, first specific binding member and capture reagent can be combined simultaneously in the assay, or they can be added and incubated individually or in combinations in a variety of sequences wherein the binding of one reagent does not prevent or inhibit the binding of another. The indicator reagent can be added simultaneously with the other reagents and test sample, but typically the indicator reagent is added after the other reagents have reacted. It will be understood by those skilled in the art that the order in which the reagents are combined as described in the following general and detailed examples should not be construed as limiting the assay method to that particular order. It is preferable, however, not to react the ASR and the first specific binding member prior to adding test sample, because the displacement of the ASR from the first specific binding member by the sample analyte may require more time than does the competitive binding between the ASR and the analyte for the first specific binding member.

In one embodiment of the present invention, predetermined amounts of ASR and a first specific binding member (e.g., an anti-analyte antibody) are contacted to a test sample. If the analyte of interest is present in the sample, then the analyte competes with the ASR for binding to the first specific binding member, or the analyte displaces the ASR from the first specific binding member. As a result, the remaining unbound or "free" ASR is proportional to the amount of analyte in the test sample.

The mixture is then contacted to a capture reagent, e.g. a second specific binding member such as an anti-ligand antibody, immobilized upon a solid phase material. Some or all of the free ASR is immobilized upon the solid phase by the capture reagent which binds to the ligand-component of the ASR. The immobilized ASR can then be detected by adding an indicator reagent comprising a third specific binding member conjugated to a label, wherein the third specific binding member is capable of binding to the analyte-component of the ASR thereby forming a detectable or measurable capture reagent/ASR/indicator reagent complex on the solid phase. The third specific binding member can be identical to the first specific binding member, and therefore in this example, the indicator reagent can be a second anti-analyte antibody conjugated to a label. The label is capable of generating a detectable signal either alone or by interaction with additional members of a signal producing system. Because the amount of immobilized ASR is directly proportional to the amount of analyte in the test sample, the amount of immobilized indicator reagent is directly proportional to the presence or amount of analyte in the test sample; the detectable signal or the rate of signal production increases as the amount of analyte in the sample increases.

In an alternative embodiment of the present invention, the capture reagent can be an analyte-specific binding member on the solid phase material, and the indicator reagent can be a labeled ligand-specific binding member. Other variations include, but are not limited to: the use of of multiple-layer solid phase devices wherein one or more of the necessary assay reagents are diffusively (i.e., capable of migrating through the solid phase) or non-diffusively (i.e., immobilized within or on the solid phase) incorporated in or on one or more of the layers; the use of teststrip materials for capillary, absorbent or chromatographic assays wherein one or more of the necessary assay reagents are diffusively or non-diffusively incorporated in or on the teststrip in one or more zones or sites; and the formation of capture reagent/ASR/indicator reagent complexes in solution, with detection of the complex either in solution or after the complex is separated from the solution by a solid phase. As known to those skilled in the art, the solid phase material can be designed to include a sufficient number of zones or layers, which contain the reagents necessary for the assay, so that the assay is substantially self-performing once a test sample is added.

Although the ASR of the present invention is especially advantageous in cases where the analyte is monovalent or too small to allow simultaneous binding to two specific binding members, its use is also advantageous in assays for larger analytes. For example, the present invention makes it unnecessary for an assay to involve two antibodies that are capable of binding to the same analyte without interfering with each other. Instead, only one anti-analyte antibody is needed to bind to the analyte-component of the ASR, and the second antibody or specific binding member need only be capable of binding to the ligand-component of the ASR to complete the formation of the binding reaction complex. This approach avoids the problems of antibody recognition of overlapping epitopes and thereby facilitates the use of polyclonal as well as monoclonal antibodies in sandwich assays. Furthermore, because the same specific binding member may be used as the ligand-component of many different analyte/ligand combinations, the same ligand-specific binding member may be used as a generic reagent in many different assays. Therefore, a single indicator reagent (e.g., labeled anti-ligand antibody) or a single solid phase system comprising a solid phase material and an immobilized capture reagent (e.g., immobilized anti-ligand antibody) can be used without modification in many different assays, thereby increasing the ease of assay performance and decreasing the cost of device manufacture.

In addition, an assay can be performed wherein a sandwich complex of capture reagent/ASR/indicator reagent is preformed and a first specific binding member is not used. This preformed complex can also be pre-attached to a solid phase material. This method is referred to as a reverse assay in which the analyte (if present in the test sample) binds to the indicator reagent and displaces it from the solid phase thereby decreasing the signal associated with the solid phase at the site of immobilized capture reagent. This method also enables the performance of a multianalyte assay, which provides separate results for each analyte, using a "generic" capture reagent such as anti-fluorescein antibody positioned at three different sites on the solid phase. For example, a different sandwich complex can be preformed at each site with the generic capture reagent and (1) a fluorescein/tetrahydrocannabinol ASR and a labeled anti-tetrahydrocannabinol antibody indicator reagent, (2) a fluorescein/cocaine ASR and a labeled anti-cocaine antibody indicator reagent, and (3) a fluorescein/opiate ASR and a labeled anti-opiate antibody indicator reagent. A test sample containing one, two or all analytes can be contacted to the solid phase thereby displacing the respective indicators and demonstrating the presence of one or more analytes by decreasing signal production at one or more sites.

Multianalyte assays can also be performed by using appropriate ligand-components and analyte-components to form a different ASR to substitute for each different analyte in the assay, e.g.s, (1) a fluorescein/cocaine ASR, a (2) rhodamine/tetrahydrocannabinol ASR, and (3) an aminomethyl fluorescein/opiate ASR. A multianalyte assay providing separate results for each analyte can thereby be performed on a single solid phase using the appropriate capture and indicator reagents.

Assays are also contemplated wherein a complex of first specific binding member/ASR/indicator reagent is preformed and reacted with the test sample, wherein analyte displaces ASR/indicator reagent subcomplex for subsequent reaction with a capture reagent. In a flow-through or test strip assay device for example, the first specific binding member/ASR/indicator reagent may be immobilized at a first reaction site and the capture reagent is immobilized at a second reaction site downstream from the first reaction site.

EXAMPLES

The following examples illustrate methods for making the ASR of the present invention as well as methods for performing the assay procedures. The examples, however, are intended only to be illustrative and not limitative upon the scope of the invention, which scope is defined solely by the claims. It will be appreciated that one skilled in the art can conceive of many other assays, including semi-quantitative and quantitative assays to which the present inventive concepts can be applied.

EXAMPLE 1

Enzyme Immunoassay for Cocaine a. Cocaine immunogen preparation

The following procedure was used to make an immunogen from which both the analyte-component of the ASR and the anti-cocaine antibody (i.e., analyte-specific binding member) were produced.

Cocaine hydrochloride (2.0 g) was dissolved in distilled water (100 ml) and concentrated hydrochloric acid (8.0 ml) and refluxed for 19 hours. After cooling to room temperature, the benzoic acid precipitated and was filtered. The filtrate was washed with chloroform to remove any remaining benzoic acid. The aqueous solution was evaporated to dryness in vacuo. The residue (ecgonine hydrochloride) was esterified by refluxing in methanolic hydrogen chloride (150 ml) for 17 hours. The solvent was removed in vacuo to yield ecgonine methyl ester as an oil.

4-(Chloromethy) benzoic acid (2.3 g) was suspended in methylene chloride (50 ml) and oxalyl chloride (2.0 ml) was added followed by dimethyl formamide (two drops). After stirring for two hours, the solvent was removed in vacuo. Dry benzene was added and removed in vacuo. Dry benzene (20 ml) was again added, and the mixture was added to ecgonine methyl ester (1.0 g). After stirring at room temperature for 19 hours, methylene chloride (300 ml) was added and the mixture was twice extracted with hydrochloric acid (1 N, 100 ml). The combined aqueous solutions were basified with potassium carbonate to pH 9 and extracted with methylene chloride twice. The combined organic layers were dried over sodium sulfate, filtered, and the solvent was removed in vacuo. Pure 4-(chloromethyl)cocaine was obtained via a silica gel column eluted with the appropriate ratio of methanol and chloroform.

The 4-(chloromethyl)cocaine (0.6 g) was dissolved in p-dioxane (25 ml) and concentrated ammonium hydroxide (25 ml). The solution was stirred at room temperature for 18 hours. The solvent was removed in vacuo to yield 4'-(aminomethyl)cocaine. The residue was dissolved in p-dioxane (15 ml) and distilled water (15 ml), and the mixture was refluxed for 21 hours. The solvent was removed in vacuo to yield 4-(aminomethyl)benzoyl ecgonine as a brown oil. The residue was dissolved in p-dioxane (4.0 ml) and distilled water (4.0 ml), and di-tert-butyldicarbonate (0.3 g) was added. The mixture was stirred at room temperature for three hours. The solvent was removed, and the 4-[(t-butoxycarbonylamino)methyl]benzoyl ecgonine was purified via a silica gel column eluted with the appropriate mixture of chloroform and methanol. Purified product was dissolved in methylene chloride (5.0 ml) and trifluoroacetic acid (5.0 ml) and stirred for two hours at room temperature. Then the solvent was removed to yield pure 4-(aminomethyl)benzoyl ecgonine bis(trifluoroacetic acid) salt.

A 25% aqueous glutaraldehyde solution was mixed with decolorizing charcoal for about five minutes and filtered through a 0.2 micron filter. An aliquot (0.65 ml) of this solution was added to each of four bottles containing aqueous bovine serum albumin (13 ml, 3.89 mg/ml) and immediately was mixed by slow rotation for 18 hours. The four solutions were combined and dialysed in a cellulose dialyzing tube (MW 12,000–14,000) against 0.06M carbonate buffer pH 9.5 at room temperature for 18 hours. After removal of the solution from the dialyzing tube, the protein concentration was determined to be 3.68 mg/ml.

The 4-(aminomethyl) benzoyl ecgonine bis(trifluoroacetic acid) salt (228 mg) [above] was dissolved in phosphate buffer (11.4 ml) containing 0.15M NaCl, pH 7.5. An aliquot (4 ml) of this solution was added to bovine serum albumin glutaraldehyde derivative (25 ml, 3.68 mg/ml) with stirring. Stirring of the mixture was continued at room temperature for 18 hours. The mixture was dialysed in a cellulose dialyzing tube (MW 12,000–14,000) against 0.1M tris(hydroxy-methyl)aminomethane (TRIS), containing 0.15M NaCl (TRIS-buffer-saline [TBS]; pH 8.0) at room temperature for 18 hours. The solution from the dialyzing tube was purified on a Sephadex® column packed and eluted with 0.15M NaCl to yield purified immunogen.

b. Cocaine/fluorescein ASR

Seventeen milligrams of the 4-(aminomethyl)benzoyl ecgonine bis(trifluoroacetic acid) salt, as prepared in Example 1.a. above, and 5-(4,6-dichloro-1,3,5-triazin-2-ylamino)fluorescein (24 mg) were dissolved in methanol (2.0 ml) and triethylamine (0.1 ml). After stirring the mixture at room temperature for 16 hours, the solvent was removed in vacuo. The resultant ASR, a cocaine-analog/fluorescein ligand complex, was purified on silica gel plates eluted with the appropriate mixture of chloroform and methanol. The ASR was then diluted to 62 nM in TBS (20 mM, pH 7.4).

c. Cocaine indicator reagent: anti-cocaine antibody/alkaline phosphatase conjugate Cocaine antibody was raised, using procedures known to those skilled in the art and the immunogen of Example 1.a. described above. The antibody was purified according to the following reactions:

The cocaine sheep serum (160 ml) was cooled to 0° C. Ammonium sulfate (160 ml, 50% of saturation) in 20 mM phosphate buffer (pH 8.0) was added, and the mixture was gently stirred at 0° C. for ten minutes. The solution was centrifuged at 10,000×g for 15 minutes at 0° C. The supernatant was poured-off and the pellet was resuspended in ammonium sulfate (25% of saturation) in 20 mM phosphate buffer (pH 8.0) at 0° C. The solution was recentrifuged at 10,000×g for ten minutes at 0° C., and the supernatant was poured-off. The solid was resuspended and centrifuged until the solid was white. Finally, the white solid was dissolved in 20 mM phosphate buffer (pH 8.0) to yield 211 milliliters of protein (15 mg/ml).

Part of the protein solution (90 ml) was diluted with 10 mM phosphate buffer (pH 8.0) until the conductance of the solution was less than or equal to the conductance of the buffer alone. Then, (diethylamino)ethyl-cellulose (DEAE, 560 g) [pre-equilibrated with 10 mM phosphate buffer (pH 8.0)] was added, and the slurry was mixed every ten minutes. After one hour, the DEAE-cellulose was filtered and washed with three half-volumes of 10 mM phosphate buffer (pH 8.0). The filtrates were combined and concentrated to 345 milliliters of protein (3.3 mg/ml).

The anti-cocaine antibody was then conjugated to alkaline phosphatase according to the following reactions.

Alkaline phosphatase (0.313 ml, 10 mg/ml) was mixed with a reaction buffer (0.656 ml) [$H_2O$ 1.5 liters, triethanolamine 14.8 g, magnesium chloride 0.480 g, and zinc chloride solution (20 ml of 14 g/100 ml distilled water), adjusted to pH 7.3 with 6N NaOH] and glutaraldehyde (0.007 ml). The mixture was stirred at room temperature for approximately 15 minutes. Anti-cocaine antibody (0.442 ml; 5.41 mg/ml) was added to the mixture which was gently stirred for two to three minutes and then allowed to stand at room temperature for another 15 minutes to form the antibody/enzyme conjugate.

Equal volumes of a TRIS quenching buffer ($H_2O$ two liters, TRIS 72.6 g, NaCl 35.04 g, magnesium chloride 1.22 g, and 60 milliliters of a zinc chloride solution [14 g/100 ml distilled water], adjusted to pH 7.3 with 6N NaOH) and the conjugate reaction mixture where then combined and stirred for five to ten minutes. The indicator reagent was then removed and diluted with conjugate buffer ($H_2O$ one liter, TBS 6 g, NaCl 6 g, magnesium chloride 0.2 g, and zinc chloride 0.01 g; pH 8.0) to obtain a 1:10 concentration.

The substrate for the indicator reagent was nitro blue tetrazolium chloride/5-bromo- 4-chloro-3-indolyl phosphate (NBT/BCIP; NBT 0.15 g and BCIP 0.5 g in one liter of $H_2O$ with amino methyl propanol 9.0 g, and magnesium chloride 0.2 g).

d. Capture reagent: anti-fluorescein antibody

Bovine serum albumin (100 mg) was dissolved in distilled water (2.0 ml) and the mixture was adjusted to a pH of 9 with 1N NaOH. Fluorescein isothiocyanate (FITC, 100 mg) in dimethylformamide (1.0 ml) was added by drops with stirring while maintaining the pH at 9 by addition of 1N NaOH. After all of the FITC was added, the mixture was stirred at room temperature for two hours. The solution was then dialysed in a cellulose dialyzing tube (MW 12,000–14,000) against 10 mM phosphate buffer (1.0 liter, pH 7) for two hours. The dialyzing tube was then dialysed against two changes of 0.9% aqueous sodium chloride (4.0 liters), for 19 hours each time, and then against three changes of 10% dimethylsulfoxide in 0.9% aqueous sodium chloride, for 24 hours each time. The final solution showed no sign of fluorescein in the dialysis solution. The resulting immunogen solution was then removed from the dialyzing tube and lyophilized to yield an orange solid. The immunogen was used according to standard procedures to produce a rabbit anti-fluorescein antibody capture reagent. The antibody was purified according to the procedure described in Example 1.c. above.

e. Capture reagent on a flow-through solid phase material

This material comprised the purified anti-fluorescein antibody (i.e., ligand-specific binding member) of Example 1.d. (100 μl of 4.5 mg/ml solution) covalently linked to carboxy-derivatized latex microparticles (Seradyne, Indianapolis, Ind.). The antibodies were coupled to the microparticles according to the following procedure.

The purified antibody (8.6 mg), microparticles (260 mg), water (20 ml), and 2-[ N-morpholino]ethane sulfonic acid (100 mM MES, 0.05 ml) were combined, and the pH of the solution was adjusted (pH 6.3 using 3N HCl or 3N NaOH). 1-Ethyl-3-(3-dimethylaminopropyl) carbodiimide (1 mg/ml EDAC, 0.1 ml) was then added, and the solution was gently stirred for 3–3.5 hours at 15°–30° C. To stop the reaction, the mixture was centrifuged at 2400–4000×g for 10 to 20 minutes. The supernatant was decanted and discarded.

The microparticles were then suspended in a volume of 0.1% Tween 20 solution (approximately equal to 0.10 times the batch size.) The centrifugation and suspension steps were then repeated. The microparticles were then suspended in buffer (conjugate buffer plus 0.1% Tween-20) and centrifuged again. The final microparticle preparation was then diluted, and 60 microliters of the preparation was deposited upon a glass fiber pad. The pad was then overcoated with a six percent fish gelatin solution and dried.

f. Cocaine immunoassay protocol

The first specific binding member (purified anti-cocaine antibody, 30 μl, 2.74 mg/ml, in 10 mM TBS) and the ASR, cocaine-analog/fluorescein ligand of Example 1.b. (100 μl), were each added to urine samples (400 μl) containing known amounts of cocaine analyte. The analyte-component of the ASR and the analyte in the test sample competed for the anti-cocaine antibody binding site so that the greater the amount of the drug in the sample the more free ASR existed in the mixture.

The mixture was immediately poured onto the solid phase material of Example 1.e. on which the ligand-specific capture reagent (anti-fluorescein antibody) had been immobilized, thereby enabling a sampling of the ASR to bind to the anti-fluorescein antibody on the solid phase. The solid phase was then washed (with a solution of guanidine hydrochloride and Tween-20).

The indicator reagent of Example 1.c. (200 μl) was contacted to the solid phase material, enabling the indicator to bind to the analyte-component of the immobilized ASR so that the ASR was sandwiched between the indicator reagent and the capture reagent on the solid phase material. If the analyte was absent from the test sample, the ASR was already sandwiched between the first specific binding member and the capture reagent, and the indicator reagent, having no place to bind, flowed through the solid phase material. The solid phase material was washed again to remove unreacted indicator reagent.

Three drops of the enzyme substrate (NBT/BCIP) were applied to the solid phase. Table 1 illustrates the results of assays performed on test samples having different cocaine concentrations. A negative (−) represents no color development, a positive (+) represents color development, and a double positive (++) represents strong color development. If a threshold amount of cocaine was present in the test sample, then the substrate reacted with the indicator reagent that was immobilized on the solid phase, and a signal was produced. If less than the threshold amount of cocaine was present in the test sample, then there was no indicator reagent on the solid phase with which the substrate could react.

TABLE 1

Cocaine Immunoassay Results

| Microparticle Dilution | Sample Concentration (ng/ml) | | | | |
|---|---|---|---|---|---|
| | 0 | 10 | 50 | 100 | 200 |
| 1:8 | − | + | ++ | ++ | ++ |
| 1:16 | − | n/p | + | ++ | ++ |

− = no color;
+ = color;
++ = strong color;
n/p = not performed

EXAMPLE 2

Enzyme Immunoassay for Morphine a. Morphine immunogen preparation

The following procedure was used to make an immunogen from which the anti-opiate antibody was produced.

Morphine-3-β-D-glucuronide (100.4 mg) was dissolved in distilled water (12 ml) with the addition of three drops of 1.0M sodium hydroxide. Sodium perborate (36 mg) was added, the pH was adjusted to 3.0, and the mixture was stirred at room temperature for 1.5 hours. Ethylene glycol (0.016 ml) was added and stirring was continued for one hour. Thyroglobulin (50.6 mg) was added, the pH was adjusted to 8.0, and after another hour, one equivalent of sodium cyanoborohydride was added. After stirring overnight, the solution was dialyzed against saline for two days. The immunogen was used, according to standard procedures, to produce sheep anti-opiate antibodies which were purified substantially in accordance with the procedure described in Example 1.c. above.

b. Morphine/fluorescein ASR

Morphine (86 mg) was dissolved in absolute ethanol (1.3 ml) upon treatment with potassium ethoxide in ethanol (0.345 ml of a 1.0M solution). Ethyl bromoacetate (57.6 mg) was added, and the mixture was stirred at room temperature under a nitrogen atmosphere for seven hours. The product was eluted with chloroform/methanol (2:1) and purified by chromatography on a silica gel thick-layer plate to give 39 mg of morphine-3-(ethoxycarbonylmethyl) ether.

The morphine-3-(ethoxycarbonylmethyl) ether (39 mg) was hydrogenated in ethanol (15 ml) and concentrated hydrochloric acid (0.009 ml) over ten milligrams of 10% palladium on carbon at an initial hydrogen pressure of 40 psi. After two hours, the product was isolated by filtration and removal of the solvent to produce 49 milligrams of 7,8-dihydromorphine-3-(ethoxycarbonylmethyl) ether.

The 7,8-dihydromorphine-3-(ethoxycarbonylmethyl) ether (49 mg) was dissolved in methanol (1.0 ml), and freshly distilled 1,2-diaminoethane (0.20 ml) was added. The mixture was allowed to stir at room temperature under a nitrogen atmosphere for 16 hours. Thorough removal of volatile materials in vacuo left 58 milligrams of 7,8-dihydromorphine- 3-[(2-aminoethyl)aminocarbonylmethyl] ether hydrochloride.

The 7,8-dihydromorphine-3-[(2-aminoethyl)aminocarbonylmethyl] ether hydrochloride (19 mg) was dissolved in methanol (0.75 ml), and 6-[4,6-dichloro-1,3,5-triazin-2-ylamino]fluorescein (27.9 mg) was added. After stirring at room temperature for 30 minutes, the mixture was diluted with dimethylformamide (0.20 ml) and streaked onto a thick-layer silica gel chromatography plate. Development with chloroform/methanol/acetic acid produced the purified morphine/fluorescein ASR. The ASR was then diluted to 200 mM in TBS (20 mM; pH 7.4).

c. Morphine indicator reagent: anti-morphine antibody/alkaline phosphatase conjugate The anti-opiate antibody was conjugated to alkaline phosphatase according to the following reactions.

Alkaline phosphatase (1.25 ml, 10 mg/ml) was mixed with reaction buffer (2.6 ml) and glutaraldehyde (0.026 ml). The mixture was stirred at room temperature for approximately 15 minutes. Purified opiate antibody (1.31 ml; 0.759 mg/ml) was added to the mixture which was gently stirred for two to three minutes and then allowed to stand at room temperature for another 15 minutes to form the antibody/enzyme conjugate.

Equal volumes of TRIS quenching buffer and the conjugate reaction mixture were then combined and stirred for five to ten minutes. The indicator reagent was then removed and diluted with buffer (the conjugate buffer of Example 1.c. plus 2% Tween-20) to obtain a 1:10 concentration. The substrate for the indicator reagent was NBT/BCIP as in Example 1.c. above.

d. Capture reagent: anti-fluorescein antibody

The capture reagent was an anti-fluorescein antibody, prepared substantially in accordance with the procedure described in Example 1.d. above.

e. Capture reagent on a flow-through solid phase material

The solid phase analytical device was prepared substantially in accordance with the procedure as described in Example 1.e. above.

f. Morphine immunoassay protocol

A first specific binding member of purified anti-morphine antibody (75 µl, 3.3 mg/ml, in 10 mM TBS) and the morphine/fluorescein ASR of Example 2.b. (100 µl) were each added to urine samples (500 µl) containing known amounts of morphine. The ASR and the analyte in the test sample competed for the first specific binding member so that the greater the amount of the drug in the sample the more free ASR existed in the mixture.

The mixture was immediately poured through a prefilter and onto the solid phase material of Example 2.e. on which the ligand-specific capture reagent had been immobilized, enabling a sampling of the ASR to bind to the ligand-specific capture reagent on the solid phase. The prefilter was removed, and the solid phase was washed with a solution of guanidine hydrochloride and Tween-20.

The indicator reagent of Example 2.c. (200 µl) was contacted to the solid phase material, enabling the indicator reagent to bind to the analyte-component of the immobilized ASR so that the ASR was sandwiched between the indicator reagent and the capture reagent on the solid phase material. If the drug was absent, the ASR was already sandwiched between the first specific binding member and the capture reagent, and the indicator reagent, having no place to bind, flowed through the solid phase material. The solid phase material was washed (with a solution of guanidine hydrochloride and Triton X-100) to remove unreacted indicator reagent.

Three drops of the enzyme substrate (NBT/BCIP) were applied to the solid phase. Table 2 illustrates the results of assays performed on test samples having different morphine concentrations. If a threshold amount of morphine was present in the test sample, then the substrate reacted with the indicator reagent that was immobilized on the solid phase, and a signal was produced. If less than the threshold amount of morphine was present in the sample, then there was no indicator reagent on the solid phase with which the substrate could react.

TABLE 2

Morphine Immunoassay Results

| Microparticle Dilution | Sample Concentration (ng/ml) | | | | | | |
|---|---|---|---|---|---|---|---|
| | 0 | 100 | 200 | 350 | 600 | 1000 | 3750 |
| 1:9 | − | − | − | ++ | ++ | ++ | ++ |

− = no color;
++ = strong color

EXAMPLE 3

Enzyme Immunoassay for Morphine Using Polystyrene Beads

The reagents of Examples 2.a. through 2.d. were used in this immunoassay.

a. Capture reagent on polystyrene beads

In this example, the anti-fluorescein antibody capture reagent of Example 2.d. was covalently linked to a solid phase of polystyrene beads (0.25 inch). The antibodies were coupled to the beads according to the following procedure.

The beads were weighed and washed overnight at room temperature in a 15% propanol solution. The beads were then washed three times in a phosphate buffered saline solution (PBS; pH 7.2). The antibodies (25 µl) and PBS (24.75 ml) were then added to the beads, and the combination was mixed overnight at room temperature. The formula had been calculated to produce about 30 micrograms of antibody per milliliter of coating solution.

The beads were again washed three times in PBS. The beads were then incubated for one hour at 40° C. in a mixture of 0.1% Triton X-100 in PBS. Following the incubation, the beads were washed three times in PBS. The beads were then incubated for one hour at 40° C. in a mixture of 3% bovine serum albumin in PBS. Following the incubation, the beads were again washed three times in PBS. The beads were then incubated for twenty minutes at room temperature in a mixture of 5% sucrose in PBS. The beads were then drained and dried overnight.

b. Morphine immunoassay protocol

Two sample solutions (200 µl each) were tested, a zero ng/ml morphine sulfate solution and a 1000 ng/ml morphine sulfate solution. A first specific binding member, the anti-opiate antibody (600 µl, Example 2.a.), was added to each solution in a test tube and gently mixed. The morphine/fluorescein ASR (200 µl, Example 2.b.) was added to each tube and mixed. A bead, bearing immobilized ligand-specific capture reagent, as prepared in Example 3.a., was added to each tube and incubated for five minutes at room temperature.

The solution was then poured-off, and the beads were washed three times. The analyte-specific indicator reagent (200 µl, Example 2.c.) was added to each tube and incubated for five minutes at room temperature. The indicator reagent was then poured-off, and the beads again were washed three times. The beads were transferred to fresh tubes, and five drops of NBT/BCIP substrate were added to each tube. Within one minute, color began to develop on the surface of the bead in the 1000 ng/ml tube. The zero ng/ml tube remained colorless.

EXAMPLE 4

Immunoassays Using Surfactant Treated Indicator Reagent

The following assays were performed using the morphine assay indicator reagent prepared substantially in accordance with the method described in Example 2.c., except that the buffer solution did not contain surfactant. Instead, the surfactant (Tween 20) was added separately to the indicator reagent to achieve about a 4.0% (w/v) concentration (i.e., approximately two drops of surfactant per one milliliter of indicator reagent.) The assay used either a surfactant-treated or an untreated indicator reagent, and the assay was performed substantially in accordance with the protocol described in Example 2.f. using a flow-through solid phase. The indicator reagent had become substantially inactive prior to the addition of the surfactant. The morphine test samples comprised a predetermined amount of morphine in human urine. The assay results are presented in Table 3.

TABLE 3

Assay Results Comparing Morphine Indicator Reagents with and without Surfactant

| Morphine (ng/ml) | without Surfactant | with Surfactant |
|---|---|---|
| 0 | − | − |
| 1000 | + | ++ |

− = no color;
+ = slight color development;
++ = strong color development

As demonstrated in Table 3, the zero morphine test sample had no color development with either indicator reagent. The morphine containing test sample produced only a slight color development, after one minute, using the indicator reagent without surfactant. Use of the indicator reagent with surfactant, however, resulted in a very strong color development that required only 15 seconds to develop.

Table 4 presents a comparison of background color development to signal color development in assays using indicator reagent preparations that contained different concentrations of surfactant. The indicator reagent used to make these preparations had appeared inactive prior to the addition of surfactant. The assays were performed substantially in accordance with the protocol described in Example 2.f. The morphine test sample comprised morphine in human urine (1000 ng/ml).

TABLE 4

Assay Results Using Different Amounts of Surfactant in the Indicator Reagent

| Surfactant in Indicator (w/v) | Background | Assay result |
| --- | --- | --- |
| 0.625% | + | ++ |
| 1.25% | + | ++ |
| 2.5% | + | ++ |
| ~4.0% | − | ++ |

− = no color;
+ = slight color development;
++ = strong color

The results, presented in Table 4, demonstrated that the high background color on the glass fiber pad occurred when lower amounts of surfactant were used. But, the addition of an approximately 4.0% concentration of Tween 20 to the indicator reagent resulted in zero background color development. It should be appreciated, however, that the amount of surfactant necessary to reactivate an indicator reagent may be greater than the amount necessary to maintain the indicator reagent's activity.

The use of the analyte-substitute reagent enables the performance of a combination competitive/sandwich assay and is applicable to virtually any binding assay. It is especially advantageous for use in assays wherein the analyte is monovalent, but it can be used wherever a sandwich or immunometric assay readout is desired. It will be appreciated that one skilled in the art can conceive of other assay methods (indirect assays, inhibition assays, etc.), as well as assays for polyvalent analytes, to which the present inventive concepts can be applied. The embodiments described and the alternative embodiments presented are intended as examples rather than as limitations. Thus, the description of the invention is not intended to limit the invention to the particular embodiments disclosed, but it is intended to encompass all equivalents and subject matter within the spirit and scope of the invention as described above and as set forth in the following claims.

What is claimed is:

1. A device for determining the presence or amount of at least one analyte of interest in a test sample, comprising:
   (a) a first reaction site having
      (i) at least one reversibly incorporated analyte-substitute reagent comprising an analyte-component conjugated to a ligand-component,
         wherein said analyte-component has at least one epitope in common with said at least one analyte of interest, and said analyte-component specifically binds to a single analyte-specific binding member, and
         wherein said ligand-component specifically binds to a ligand-specific binding member but does not specifically bind to an analyte-specific binding member, and
      (ii) at least one immobilized first analyte-specific binding member which specifically binds an epitope present on both said at least one analyte of interest and said analyte-component of said analyte-substitute reagent,
   wherein in the presence of said at least one analyte of interest, a mixture of analyte/first analyte-specific binding member complex, analyte-substitute reagent/first analyte-specific binding member complex, and unbound analyte-substitute reagent is formed and the amount of unbound analyte-substitute reagent increases as the amount of said at least one analyte of interest increases;
   (b) a second reaction site distinct from said first reaction site having
   at least one reversibly incorporated indicator reagent each comprising a label capable of producing a detectable signal, wherein said label is conjugated to a second specific binding member which directly or indirectly specifically binds said unbound analyte-substitute reagent; and
   (c) a third reaction site distinct from said first and second reaction sites having
   at least one directly or indirectly immobilized capture reagent comprising a third specific binding member which specifically binds said analyte-substitute reagent,
   wherein said at least one capture reagent and said at least one indicator reagent form a directly or indirectly bound detectable complex with said unbound analyte-substitute reagent which indicates the presence or amount of said at least one analyte, and
   wherein when said capture reagent specifically binds said analyte-component then said indicator reagent specifically binds said ligand-component, and when said capture reagent specifically binds said ligand-component then said indicator reagent specifically binds said analyte-component.

2. The device according to claim 1, wherein said first, second, and third reaction sites are nonoverlapping zones on a chromatographic test strip.

3. The device according to claim 1, wherein said first, second, and third reaction sites are individual layers of a multiple layer device.

4. A chromatographic test device for determining the presence or amount of at least one analyte of interest in a test sample, comprising:
   (a) a first reaction site having
      (i) at least one reversibly incorporated analyte-substitute reagent comprising an analyte-component conjugated to a ligand-component,
         wherein said analyte-component has at least one epitope in common with said at least one analyte of interest, and
         wherein said ligand-component specifically binds to a ligand-specific binding member but does not specifically bind to an analyte-specific binding member, and
      (ii) at least one immobilized first analyte-specific binding member which specifically binds an epitope present on both said at least one analyte of interest and said analyte-component of said analyte-substitute reagent, wherein in the presence of said at least one analyte of interest, a mixture of analyte/first analyte-specific binding member complex, analyte-substitute reagent/first analyte-specific binding member complex, and unbound analyte-substitute reagent is formed and the amount of unbound analyte-substitute reagent increases as the amount of said at least one analyte of interest increases;

(b) a second reaction site distinct from and downstream from said first reaction site having at least one reversibly incorporated indicator reagent each comprising a label capable of producing a detectable signal, wherein said label is conjugated to a second specific binding member which directly or indirectly specifically binds said unbound analyte-substitute reagent; and (c) a third reaction site distinct from and downstream from said first and second reaction sites having at least one directly or indirectly immobilized capture reagent comprising a third specific binding member which specifically binds said analyte-substitute reagent, wherein said at least one capture reagent and said at least one indicator reagent form a directly or indirectly bound detectable complex with said unbound analyte-substitute reagent which indicates the presence or amount of said at least one analyte, and wherein when said capture reagent specifically binds said analyte-component then said indicator reagent specifically binds said ligand-component, and when said capture reagent specifically binds said ligand-component then said indicator reagent specifically binds said analyte-component.

* * * * *